(12) United States Patent
Zinnen et al.

(10) Patent No.: US 6,455,736 B1
(45) Date of Patent: Sep. 24, 2002

(54) PROCESS FOR PREPARATION OF PHARMACEUTICALLY DESIRED SERTRALINE AND SERTRALINE ANALOGS

(75) Inventors: Herman A. Zinnen, Evanston; Mark J. Gattuso, Palatine, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/705,536

(22) Filed: Nov. 3, 2000

(Under 37 CFR 1.47)

Related U.S. Application Data

(63) Continuation-in-part of application No. 09/255,300, filed on Feb. 22, 1999, now Pat. No. 6,162,949, which is a continuation-in-part of application No. 08/357,910, filed on Dec. 16, 1994, now Pat. No. 5,889,186.

(51) Int. Cl.[7] ............................................. C07C 209/88
(52) U.S. Cl. ..................... 564/304; 558/418; 564/302; 564/308
(58) Field of Search ................................. 564/304, 302, 564/308; 558/418

(56) References Cited

U.S. PATENT DOCUMENTS

| | | | |
|---|---|---|---|
| 2,985,589 A | 5/1961 | Broughton et al. | 210/34 |
| 4,536,518 A | 8/1985 | Welch, Jr. et al. | 514/647 |
| 4,556,676 A | 12/1985 | Welch, Jr. et al. | 514/554 |
| 5,104,899 A | 4/1992 | Young et al. | 514/646 |
| 5,889,186 A | 3/1999 | Gattuso | 564/304 |

FOREIGN PATENT DOCUMENTS

WO   WO 99-57089   11/1999

OTHER PUBLICATIONS

Skrebnik, Ramachandran & Brown, *J. Org. Chem.* 53, 2916, 1988.

Gao & Sharpless, *J. Org. Chem* 53, 4081, 1988.

E. J. Corey and G.A.. Reichard, *Tetrahedron Letters,* 30, No. 39, 5207 (1989).

Schneider and Goergens, *Tetraedron: Asymmetry,* No. 4, 525, 1992.

W. M. Welch, Jr., et al., *Journal of Medicinal Chemistry,* vol. 27, No. 11, p. 1508, (1984).

*Primary Examiner*—Richard L. Raymond
(74) *Attorney, Agent, or Firm*—John G. Tolomei; Frank S. Molinaro; Maryann Maas

(57) ABSTRACT

Improved processes for preparation of sertraline or sertraline analogs in high enantiomeric purity centers on resolution using simulated moving bed chromatography of isomeric racemic sertraline or sertraline analogs. Resolution is effected with high enantiomeric purity, and the undesired enantiomer may be racemized and recycled to the resolution phase to avoid loss.

8 Claims, 2 Drawing Sheets

PROCESS FOR PREPARATION OF PHARMACEUTICALLY DESIRED SERTRALINE AND SERTRALINE ANALOGS

CROSS REFERENCE TO RELATED APPLICATIONS

This application is a continuation-in-part of our application, application Ser. No. 09/255,300, filed Feb. 22, 1999, now U.S. Pat. No. 6,162,949, which in turn is a continuation-in-part of application Ser. No. 08/357,910 filed Dec. 16, 1994, now U.S. Pat. No. 5,889,186 all of which are hereby incorporated by reference.

BACKGROUND OF THE INVENTION

At the molecular level biological systems are highly asymmetric; enzymes, proteins, polysaccharides, nucleic acids, and many other fundamental components of life are present in optically active form. The implications of this are profound; as a general proposition the interaction of a chiral molecule with an optically active site is a diastereomeric interaction, and the two enantiomers properly should be viewed as distinct compounds capable of acting in different ways. (R)-Asparagine has a bitter taste, whereas the (S)-isomer is sweet. It has been known for some time that for medicinals having at least one chiral center the pharmacological effectiveness of the enantiomers of the racemic mixture may differ substantially, and in some cases the pharmacological action itself may differ. An extreme example is provided by propranolol, where the major pharmacological effect of the (R)-isomer is as a contraceptive, whereas the major pharmacological effect of the (S)-isomer is as a beta-blocker.

Although the recognition of the desirability of using the pharmacologically and pharmaceutically more acceptable enantiomer is old, nonetheless the use of optically pure medicinals generally is relatively new, simply because of the difficulty and cost of resolution of the racemic mixture and/or the difficulty and cost of asymmetric synthesis of the desired enantiomer. The importance of stereochemical purity may be exemplified by (S)-propranolol, which is known to be 100 times more potent as a beta-blocker than its (R)-enantiomer. Furthermore, optical purity is important since certain isomers actually may be deleterious rather than simply inert. For example, the R-enantiomer of thalidomide was a safe and effective sedative when prescribed for the control of morning sickness during pregnancy. However, S-thalidomide was discovered to be a potent teratogen leaving in its wake a multitude of infants deformed at birth.

With recent chemical advances, especially in asymmetric synthesis, has come both an increase in the feasibility of selectively preparing the desired enantiomer of a given chiral medicinal, as well as increasing pressure on the pharmaceutical industry to make available only that enantiomer. Instructive examples, pertinent to the subject matter of this invention, are the antidepressant cis-(1S)(4S)-N-methyl-4-(3,4-dichlorophenyl)-1,2,3,4-tetrahydro-1-naphthalenamine, (hereinafter, "sertraline, or where racemic, "racemic sertraline"), which has Formula I, and the class of compounds (hereinafter, "sertraline analogs" or where racemic, "racemic sertraline analogs") having Formula II.

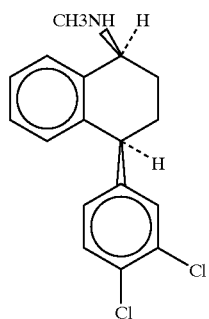

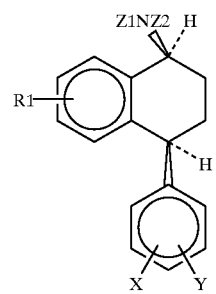

Thus, there is described in U.S. Pat. Nos. 4,536,518, and 4,556,676 to W. M. Welch, Jr., as well as in the paper of W. M Welch, Jr. et. al., *Journal of Medicinal Chemistry*, Vol. 27, No. 11, p. 1508, (1984) a multi-step method for synthesizing pure cis-(1S)(4S)-N-methyl-4-(3,4-dichlorophenyl)-1,2,3,4-tetrahydro-1-naphthalenamine. An important synthetic step involves reduction of a precursor immine to the corresponding amine, which reduction results in a mixture of the cis and trans isomers in the form of a racemate. This isomeric mixture is then separated by chromatography on silica gel or by fractional crystallization of the hydrochloride salts. The cis racemate amine free base is then classically resolved with an optically-selective precipitant acid, as is known in the art, to yield sertraline.

The foregoing are examples of conventional synthesis and separation, as are known in the art, relevant to sertraline in which isomer separation of a sertraline precursor is performed by chromatography or by crystallization, and enantiomer separation leading to the final target medicinal sertraline is performed by optically-selective precipitation. Another approach of resolving a precursor is exemplified by the work of Schneider and Goergens, *Tetrahedron: Asymmetry*, No. 4, 525, 1992. These authors effected enzymatic resolution of 3-chloro-1-phenyl-1-propanol (CPP) via enzymatic hydrolysis of the racemic acetate in the presence of a lipase from *Pseudomonas fluorescens* under close pH control with a phosphate buffer. The hydrolysis was halted after about 50% conversion to afford the R-alcohol while leaving unchanged the S-acetate, which subsequently could be hydrolyzed with base to the S-alcohol. From the enantiomerically pure alcohols the enantiomerically pure serotonin-uptake inhibitors fluoxetine (whose racemate is available as Prozac™), tomoxetine, and nisoxetine could be prepared.

The Schneider and Goergens approach highlights a characteristic of methods based on resolution of a racemate, whether the racemate is that of a precursor or of a final medicinal compound, which requires our attention. The authors used both the R- and S-CPP to prepare both R- and S-fluoxetine in high optical purity, although one enantiomer is substantially more desirable than the other (see U.S. Pat. No. 5,104,899, supra). Consequently, in practice only, the more desirable enantiomer will be utilized, either in subsequent synthesis or as the final chiral medicinal. There then results the economic burden of discarding the less desirable (or even undesirable) enantiomer, whether of a precursor or of a final medicinal. Thus, it is imperative to somehow utilize the undesired enantiomer which results from resolution. Stated concisely, incident to a method of preparing medicinals of high optical purity based on resolution of a racemate of a raw material, intermediate or of a final medicinal, is the requirement of utilizing the unwanted enantiomer produced as a byproduct of the resolution stage. For a final medicinal compound, perhaps the most desirable utilization of the unwanted enantiomer would be to racemize it and recycle the racemate back to the separation stage; this application is directed precisely to such a process.

SUMMARY OF THE INVENTION

The purpose of the present invention is to present a process for the preparation of sertraline and for preparation of the more desirable enantiomers of sertraline analogs. One embodiment comprises separation of isomeric racemic sertraline or isomeric racemic sertraline analogs by simulated moving bed chromatography using a chiral or non-chiral adsorbent to afford at least one substantially pure racemic sertraline isomer or racemic sertraline analog isomer, resolution of a sertraline isomer racemate or sertraline analog isomer racemate by simulated moving bed chromatography using a chiral adsorbent to afford at least one substantially pure sertraline enantiomer pair or sertraline analog enantiomer pair, resolution of a sertraline enantiomer pair or sertraline analog enantiomer pair by simulated moving bed chromatography using a chiral adsorbent to afford substantially pure sertraline or at least one substantially pure sertraline analog, and conversion of less desirable isomers and/or enantiomers to a mixture of isomeric racemic sertraline or sertraline analogs, with recycle to the an appropriate resolution stage. In a specific embodiment cis-(1S)(4S)-N-methyl-4-(3,4-dichlorophenyl)-1,2,3,4-tetrahydro-1-naphthalenamine is utilized as the substantially pure sertraline enantiomer.

DESCRIPTION OF THE INVENTION

The present invention is better understood in the context of synthetic routes to sertraline and sertraline analogs, derived from the related precursor class of compounds having the formula III, generally referred to as "tetralones"

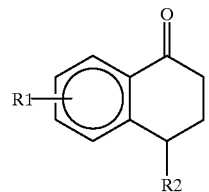

where R1=hydrogen, fluoro, chloro, bromo, trifluoromethyl, and alkoxy of 1 to 3 carbon atoms, R2 has the structure

where X and Y are selected from the group consisting of hydrogen, fluoro, chloro, bromo, trifluoromethyl, cyano, and alkoxy of 1 to 3 carbon atoms, with at least one of X or Y being other than hydrogen. In a preferred embodiment, R1 is hydrogen, X is Cl, and Y is Cl.

The specific features of one generalized preparative route to sertraline and sertraline analogs, depicting only those features of central interest here, are given in equation (1):

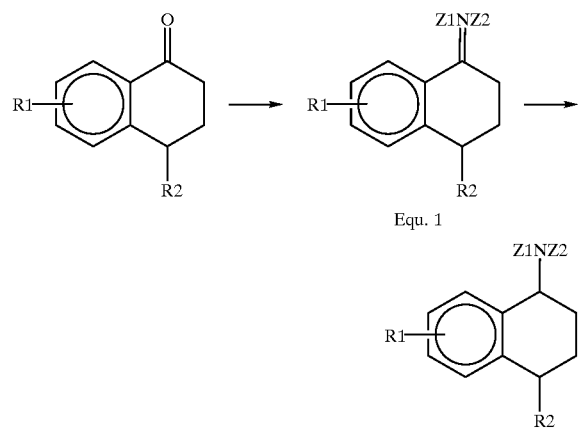

Equ. 1

The conversion shown in Equation 1 whereby chiral tetralones are transformed to the corresponding immines, followed by reduction thereof to N-substituted-(disubstituted phenyl)-1,2,3,4-tetrahydro-1-naphthaleneamines can be accomplished by methods known in the art. Unfortunately, such a synthetic route has the undesirable result of producing a mixture of cis and trans amine isomers in the form of a racemate upon reduction of the immine function, rather than the desired cis-N-substituted-(disubstituted-phenyl)-1, 2,3,4-tetrhydro-1-naphthaleneamines. Thus, this synthesis requires separation of the isomeric sertraline racemate or isomeric sertraline analog racemate to produce the desired cis racemic sertraline or cis racemic sertraline analogs. This can then be followed by another separation of the cis racemic sertraline or cis racemic sertraline analogs to yield a cis sertraline enantiomer pair or a cis sertraline analog enantiomer pair. Then the desired sertraline or chiral sertraline analogs can be obtained from separation of the enantiomer pairs.

Figure 1:
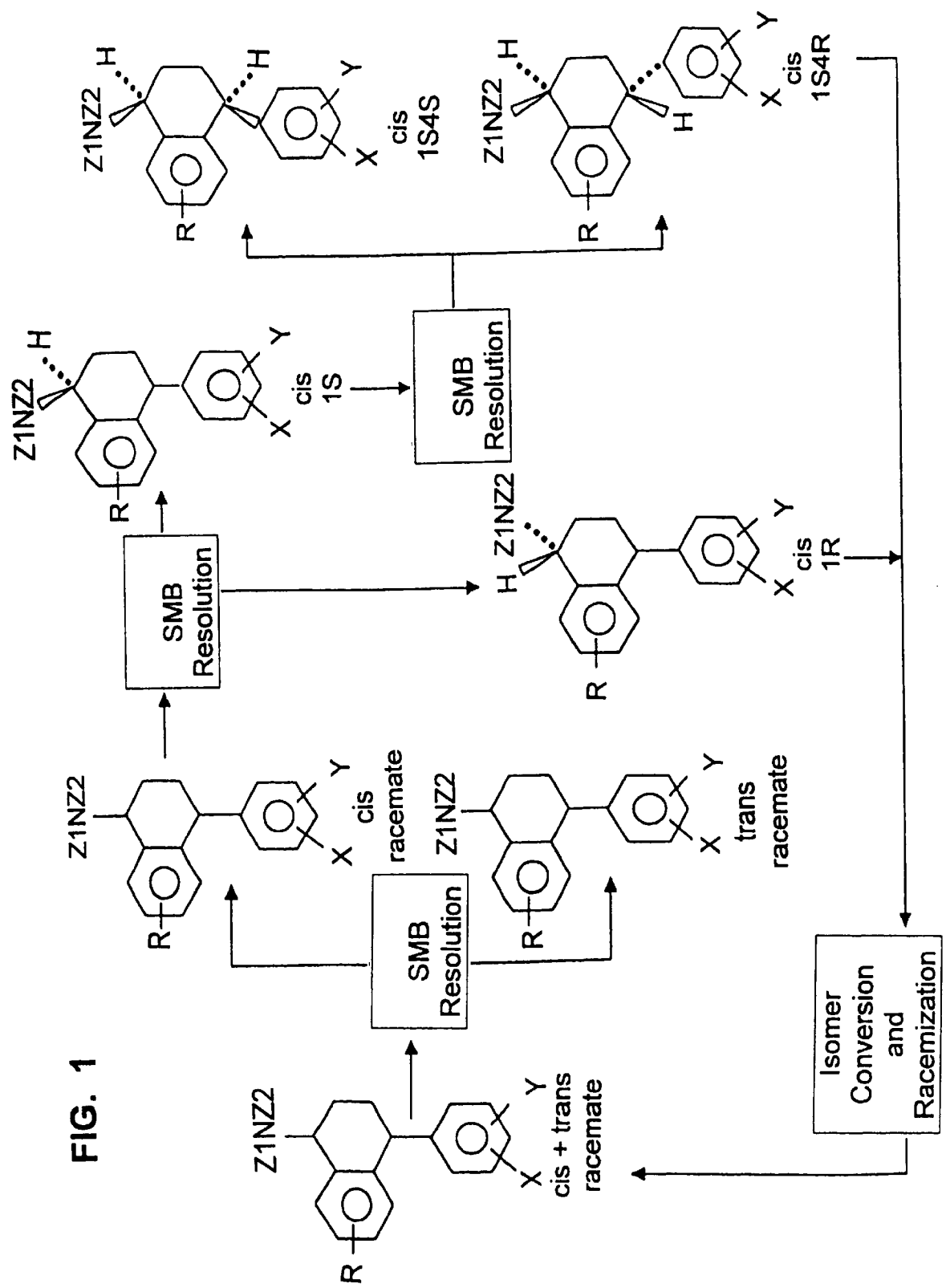
FIG. 1 represents a process flow for the preparation of sertraline or sertraline analogs utilizing simulated moving bed chromatography to resolve isomeric racemic sertraline or isomeric racemic sertraline analogs into sertraline or sertraline analogs, and recycle of the other isomers and enantiomers to the resolution stage.
Figure 2:
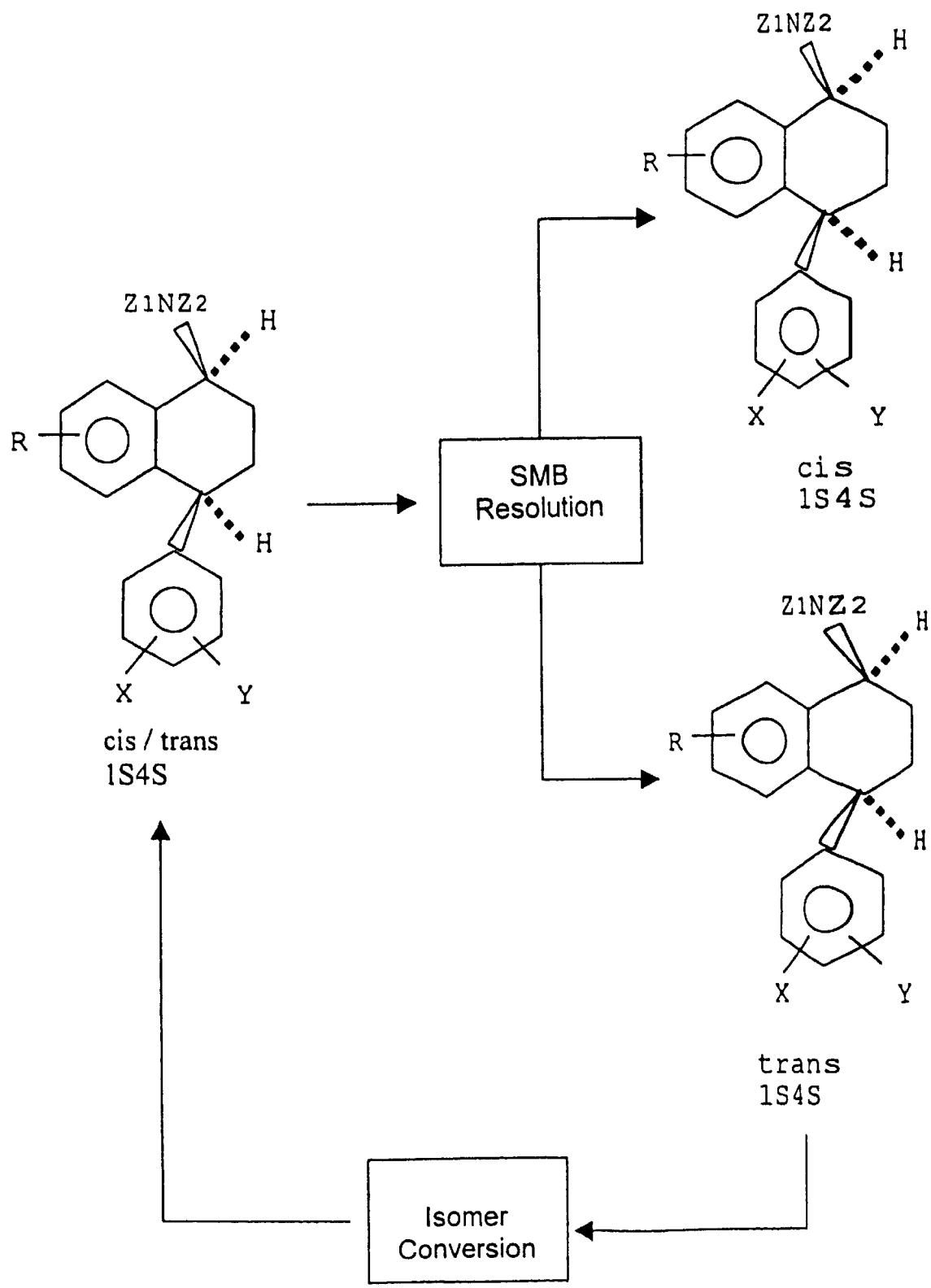
FIG. 2 represents a process flow for the preparation of sertraline or sertraline analogs utilizing simulated moving bed chromatography to resolve isomeric sertraline or sertraline analogs into sertraline or sertraline analogs, and recycle of the other isomers to the resolution stage.

An advantage of our invention for preparing sertraline or chiral sertraline analogs is that racemic sertraline or sertraline analogs and their enantiomer pairs may be resolved without the need for expensive optically selective precipitating agents, and the undesired sertraline or sertraline analog enantiomers can be converted back to racemic sertraline or sertraline analogs and recycled to a resolution stage, as illustrated in FIGS. 1 and 2. Moreover, since simulated moving bed chromatography is a continuous process, quality control can be more effective and can be continuous in the context that separation parameters may be changed incrementally at frequent intervals.

Before describing the specifics of the processes in FIGS. 1 and 2 we will briefly review simulated moving bed chromatography. The advantages of the moving bed of adsorbent in a countercurrent separation process have long been recognized. Because of the difficulty of an actual moving adsorbent bed, a flow scheme has been devised which maintains the process features of continuous countercurrent flow of fluid and solid without the actual movement of solids-i.e., a simulated moving bed.

In simulated moving bed processes the adsorption and desorption operations are continuously occurring which allows both continuous production of an extract and a raffinate stream with the continual use of feed and desorbent streams. A preferred embodiment of this process utilizes what is known in the art as the simulated moving bed countercurrent flow system. The operating principals and sequence of such a flow system are described in U.S. Pat. No. 2,985,589.

Simulated moving bed chromatography is a flow scheme which has been devised which maintains the process features of continuous countercurrent flow of fluid and solid without actual movement of the solid. The simulated moving bed technique has been described in R. A. Meyers, *Handbook of Petroleum Refining Processes*, pages 8–85 to 8–87, McGraw-Hill Book Company (1986). The technique has been applied commercially to a number of processes such as a separation of p-xylene from $C_8$ aromatic isomers, the separation of linear paraffins from branched-chain and cyclic hydrocarbons, and a process to separate fructose and glucose from mixtures thereof, to name just a few.

Simulated moving bed chromatography may be readily applied to resolution of racemates simply by using a chiral adsorbent. See, e.g., M. Negawa and F. Shoji, *J. Chrom.*, 590, (1992), 113–7; M. J. Gattuso, B. McCullough, and J. W. Priegnitz presented at Chiral Europe '94 Symposium, Spring Innovations, Nice, France, Sep. 19–20, 1994.

A necessary feature of our invention is the adjustment of separation conditions to optimize the production of the desired enantiomer of high enantiomeric purity, i.e., optimize the formation of substantially pure desired enantiomer. By "substantially pure" is meant material of at least 95% enantiomeric purity, preferably at least 97% enantiomeric purity.

A specific embodiment involves the isomer conversion of undesired isomers and racemization of undesired enantiomers obtained by SMB isomer separation and resolution of the various mixtures. Any isomer conversion and racemization means proceeding at high yield and with good selectivity will suffice. Satisfaction of these requirements maximizes the utilization of racemic starting material while minimizing the overall process cost.

Referring to FIG. 1, the cis and trans amine isomers of sertraline or sertraline analog racemates are separated with the use of simulated moving bed chromatography using a chiral or non-chiral adsorbent to afford substantially pure cis racemic sertraline or cis racemic sertraline analogs. In a second step the cis racemic sertraline or cis racemic sertraline analogs are separated with the use of simulated moving bed chromatography using a chiral adsorbent to afford sertraline enantiomer pairs or sertraline analog enantiomer pairs. The desired enantiomer can then be separated from the enantiomer pair with the use of simulated moving bed chromatography using a chiral adsorbent to afford sertraline or chiral sertraline analogs. In one or several steps the undesired isomers can then be converted to mixtures of cis and trans isomers by isomerization and the undesired enantiomers can be racemized, with subsequent recycle an appropriate preceding resolution stage. FIG. 2 illustrates an example of a process in which sertraline or sertraline analogs are produced with the use of simulated moving bed chromatography using a chiral adsorbent to afford separation of enantiomers followed by isomer conversion without racemization, and recycle of the resulting cis and trans isomers of the undesired enantiomer to the separation stage.

What is claimed is:

1. In a process for preparation of compounds formula II

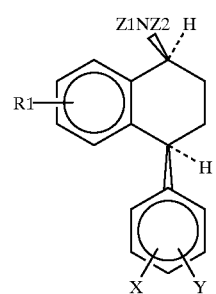

by selectively converting a compound of formula IV to II

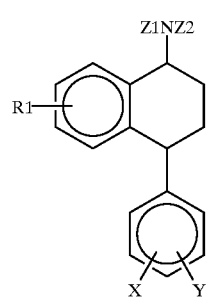

where $R_1$ is selected from the group consisting of hydrogen, fluoro, chloro, bromo, trifluoromethyl, and alkoxy having from 1 to 3 carbon atoms, where X and Y are independently selected from the group consisting of hydrogen, fluoro, chloro, bromo, trifluoromethyl, cyano, and alkoxy having from 1 to 3 carbon atoms with at least one of X or Y being other than hydrogen, and where Z1 and Z2 are selected from the group consisting of hydrogen and alkyl having from 1 to 3 carbon atoms, the improvement comprising the selective preparation of II of at least 95% enantiomeric purity by:
 a) resolving cis and trans racemic IV in a first resolution zone by simulated moving bed chromatography using a non-chiral or chiral adsorbent to afford a first isomer of racemic IV in at least 95% enantiomeric purity and a second isomer of racemic IV;
 b) resolving the first isomer of racemic IV in a second resolution zone by simulated moving bed chromatography using a chiral adsorbent to afford a first enantiomer pair of II in at least 95% enantiomeric purity and a second enantiomer pair of II;

c) resolving the first enantiomer pair of II in a third resolution zone by simulated moving bed chromatography using a chiral adsorbent to afford a first enantiomer of II in at least 95% enantiomeric purity and a second enantiomer of II; and d) racemizing the second enantiomer pair of II, and recycling to the first or second resolution zone.

2. The process of claim 1 wherein $R_1$ is hydrogen.

3. The process of claim 1 wherein X is chlorine.

4. The process of claim 1 wherein Y is chlorine.

5. The process of claim 1 wherein Z1 is hydrogen.

6. The process of claim 1 wherein Z2 is methyl.

7. The process of claim 1 further comprising isomerizing at least a portion of the second isomer of racemic IV and recycling to the first resolution zone.

8. The process of claim 1 further comprising racemizing the second enantiomer of II and recycling to a resolution zone selected from the group consisting of the first, second and third resolution zones.

* * * * *